United States Patent [19]

Meresz et al.

[11] 4,018,844

[45] Apr. 19, 1977

[54] LONG CHAIN INTERNALLY UNSATURATED ALKENES

[76] Inventors: Otto Meresz, 8 Wallingford Road; Cecilia Mozsgai, 10 Sunny Glenway No. 103, both of Don Mills, Ontario, Canada

[22] Filed: Sept. 22, 1975

[21] Appl. No.: 615,739

Related U.S. Application Data

[62] Division of Ser. No. 368,960, June 11, 1973, Pat. No. 3,932,616.

[30] Foreign Application Priority Data

June 26, 1972 United Kingdom ............. 29835/72

[52] U.S. Cl. .......................... 260/677 R; 204/59 R; 260/680 R; 260/681; 260/682
[51] Int. Cl.² ................... C07C 11/02; C07C 11/12

[58] Field of Search ................... 260/677 R, 680 R

[56] References Cited

OTHER PUBLICATIONS

Carlson et al., "Science", 174 (1971), No. 4,004, pp. 76 to 78 (Oct. 1, 1971).

*Primary Examiner*—Herbert Levine
*Attorney, Agent, or Firm*—Robert G. Hirons

[57] ABSTRACT

Long chain alkenes are produced by electrolyzing an organic solution containing a mixture of short chain carboxylic acid and a larger chain carboxylic acid, one of which is unsaturated. Many of the products so formed are useful as insect attractants.

2 Claims, No Drawings

LONG CHAIN INTERNALLY UNSATURATED ALKENES

This is a division, of application Ser. No. 368,960, filed June 11, 1973 now U.S. Pat. No. 3,932,616.

FIELD OF THE INVENTION

This invention relates to synthesis of long chain alkenes, and alkenes which can be so produced.

BRIEF DESCRIPTION OF THE PRIOR ART

Known methods of preparing alkenes include the Wittig reaction, wherein a carbonyl compound is reacted with an organophosphorus compound, thus:

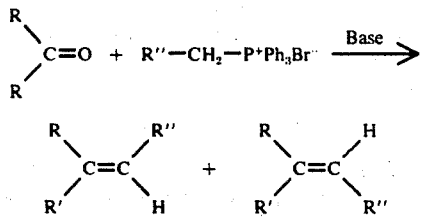

where Ph is phenyl, and R, R' and R'' are alkyl, aryl or hydrogen. As with other methods for making internal alkenes, a mixture of cis and trans geometrical isomers is formed, which is difficult to separate, and the process is expensive.

SUMMARY OF THE INVENTION

This invention produces long chain, internal alkenes by electrolysing a solution of two or more carboxylic acids, one of which has unsaturation. If a pure geometrical isomer of internally unsaturated acid is used, the same geometrical isomer of inernal alkene is produced. Internal alkenes, many of which are novel, with valuable properties are thus produced.

This synthesis is similar to the Kolbe electrolytic synthesis, in which a carboxylic acid is electrolysed, eliminating carbon dioxide at the cell anode, thus:

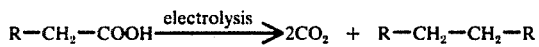

The process of the invention however uses mixtures of acid starting materials, and proceeds in a manner not predictable from the prior teachings of Kolbe synthesis. From acids of formulae R.COOH and R'.COOH one would expect Kolbe synthesis to yield a mixture of coupled products R-R, R'-R' and R'R. The stronger the acid, R-COOH, the more coupled product R-R should be formed. However in practice the yield of crosscoupled product R'-R is greater than predicted, and at least one other product, which can be represented as R'H, i.e. an elimination product, is also formed to an appreciable extent. These factors can have significant practical advantages.

The long chain internal alkenes which can be produced have from 8–40 carbon atoms, preferably from 9 to 25 carbon atoms. They are preferably made from a short chain saturated acid (acetic acid, propionic acid, butyric acid, pentanoic acid, heptanoic acid, etc.), and a longer chain ($C_7$–$C_{23}$) unsaturated acid, which acids can be synthetic but are in many cases naturally occurring. Examples of useful naturally occurring acids are decylenic acid ($C_{10}$), dodecylenic ($C_{12}$), tetradecylenic ($C_{14}$), palmitoleic ($C_{16}$), oleic ($C_{18}$), gadolenic ($C_{20}$), cetoleic ($C_{20}$), erucic ($C_{22}$) and nervonic ($C_{24}$). These all have one unsaturation and cis configuration. Elaidic acid, the trans isomer of oleic, is also useful.

DESCRIPTION OF THE PREFERRED EMBODIMENT

It is preferred to use an excess (2–10 fold, preferably 4–5 fold) of short chain acid, despite the fact that short chain acids have larger dissociation constants, i.e., are stronger, since this appears to favour the formation of cross-coupled product, without promoting undesirable side reactions. It is also preferred to carry out the electrolysis in an organic solvent capable of maintaining carboxylate ions in solution and thus becoming conducting, such as methyl alcohol, ethyl alcohol, cellosolves, ethylene glycol dimethyl ether, pyridine, etc.; a non-conductive solvent such as petroleum ether, cyclohexane, hexane, and other non-aromatic hydrocarbon liquids can also be present in admixture with the conducting solvent. Catalytic amounts of a base such as sodium methoxide are also preferably present, to improve the recoverable yield of desired products. The reaction medium is generally acidic, which condition appears to favour formation of cross-coupled product. The preferred slightly acidic conditions are maintained as the electrolysis proceeds by the metal ions derived from the catalyst, e.g., sodium methoxide, causing further acid dissociation. During electrolysis, the metal cations, e.g., $Na^-$ are discharged on the cathode, and the metal Na so formed reacts with the reaction medium to produce further sodium methoxide, which then causes further acid dissociation to give carboxylate ions, or reacts with the acids to form carboxylate ions directly. The desired coupled and elimination products are formed from the carboxylate ions. This controlled ionization procedure in electrolytic reactions, controlled by a base catalyst, is known as the "salt deficit method". Insteak of sodium methoxide, one can use other alkali and alkaline earth metal compounds which produce carboxylate ions soluble in the chosen reaction medium. Sodium, potassium and lithium compounds are preferred.

The cathode used in the process can be of substantially any inert material, preferably a metal such as platinum, nickel, palladium, stainless steel or the like. The anode is preferably metal, especially platinum.

The long chain alkenes have many uses, both per se and as intermediates for producing other industrially important products. They are all more or less viscous liquids, miscible with other organic oils to form lubricants. They are generally colorless and non-straining and can be used as solvents for waxes and organic greases. They are useful as intermediates for making perfumes. Cleavage of the alkene at the double bond, to form two aldehydic molecules, is achieved by reacting the alkene with ozone, followed by reduction with zinc. When the product has unsaturation at the 9-position, one product thereof is nonyl aldehyde which is a commercially important perfume and intermedite for other perfumes. The other product of this reaction is also an aldehyde, and substantially all aldehydes in the range $C_9$–$C_{20}$ are useful as ingredients for perfumes.

Many long chain alkenes of this invention show activity as pheromones, e.g. as insect attractants. For example, the compound cis-9-tricosene is the sex attractant of the common house fly (Musca domestica) and can readily be obtained by electrolysing a mixture of the naturally occurring fatty acid erucic acid, and propionic acid, or by electrolysing a mixture of oleic and heptanoic acids. Pheromonic activity has been demonstrated also for the compounds listed in Table 1 hereof, which follows. The cross coupled product from stearic acid and vinylacetic acid (example 19) is 1-eicosene which is a natural component of human skin lipids and is a repellent to Yellow Fever mosquitoes.

The synthesis of cis-9-triscosene from erucic acid according to this invention is an especially preferred embodiment. The elimination product is cis-9-uncosene (cis-9-heneicosene), which has a synergistic effect upon cis-9-tricosene as a sex attractant for the house fly. Such synergism is demonstrated by the increased activity of such mixture over that of the cis-9-tricosene alone as isolated from house flies. The synergism is exhibited by mixtures of cis-9-tricosene and cis-9-uncosene in proportions obtained directly from the process of the invention, i.e,. from about 60–80% by weight cis-9-tricosene and from about 40–20% by weight cis-9-uncosene. Thus by this process one obtains a synergistic insect attractant mixture in a one-step synthesis. Cis-9-hereicosene can also be produced as the major product from oleic and valeric acids by the process of the invention.

The products of the invention, being internally unsaturated, can be readily converted to other products by addition reaction. They can be oxidized to long chain epoxides, which have activity as pheromones. They provide backbones for graft copolymerization to form high polymers.

The products can have functional groups and substituents, formed from substituted starting products. These include lower alkyl, lower cycloalkyl, lower aryl, hydroxy, halogen, lower alkoxy, lower cycloalkoxy, aryloxy and lower acryloxy. The invention is not limited to mono-unsaturated starting materials and products, but applies to polyunsaturated carboxylic acids, for example linoleic acid, linolenic and eleostearic acids. Epoxides formed from such polyunsaturates are useful for making epoxy resins.

The invention is described in the following examples.

EXAMPLE 1

A solution containing erucic acid (10.18 g), propionic acid (10.5 g) and sodium metal (0.1 g) in methyl alcohol (150 ml) and petroleum ether (100 mls) was electrolysed (2-3 amps current) between platinum electrodes at 20°–25° C until the reaction mixture became slightly alkaline. This took about five hours. The reaction mixture was evaporated eliminating the butane formed, and the residue distilled in high vacuum to give a product $b_{0.05}$ 145–160°, the NMR spectrum of which was consistent with the structure of cis-9-tricosene. Gas chromatographic analysis indicated that the product contained approximately 10–30% of another component which was later characterised as cis-9-heneicosene. The yield of the product (6.24 g) calculated as cis-9-tricosene was 64.6%. The weight ratio of cis-9-tricosene to cis-9-heneicosene in the product was about 7:3.

EXAMPLES 2–20

Following the procedure of Example 1, using the same solvents, catalysts and electrodes in substantially the same quantities, different alkene products was formed from various acids combinations, as shown in Table 1.

TABLE 1

| Example | Short Chain Acid | Long Chain Acid | Cross Coupled Product | Boiling Point (0.05 mm. Hg.) | Refractive Index $n_D^{25°}$ | Yield (%) | Elimination Product (%) |
|---|---|---|---|---|---|---|---|
| 2 | Acetic | Erucic | cis-9-docosene | 120–130° | 1.4502 | 40–45 | 10–15 |
| 3 | Butyric | Erucic | cis-9-tetracosene | 136–146° | 1.4516 | 50–55 | 5–10 |
| 4 | iso Butyric | Erucic | 2-methyl-cis-14-tricosene | 142–150° | 1.4510 | 60–65 | 45–50 |
| 5 | Valeric | Erucic | cis-9-pentacosene | 142–166° | 1.4533 | 65–70 | 10–15 |
| 6 | iso Valeric | Erucic | 2-methyl-cis-15-tetracosene | 135–145° | 1.4521 | 50–58 | 25–30 |
| 7 | Acetic | Oleic | cis-9-octadecene | 102–112° | 1.4454 | 35–40 | 15–20 |
| 8 | Propionic | Oleic | cis-9-nonadecene | 120–130° | 1.4472 | 55–60 | 25–30 |
| 9 | Butyric | Oleic | cis-9-eicosene | 112–116° | 1.4454 | 65–70 | 10–15 |
| 10 | Valeric | Oleic | cis-9-heneicosene | 122–132° | 1.4491 | 70–75 | 10–15 |
| 11 | iso Valeric | Oleic | 2-methyl-cis-11-eicosene | 116–126° | 1.4476 | 65–70 | 8–12 |
| 12 | Heptanoic | Oleic | cis-9-tricosene | 130–132° | 1.4541 | 70–75 | 5–8 |
| 13 | 3-Chloropropionic | Oleic | 1-chloro-cis-10-nonadecene | 115–130° | 1.4595 | 75–80 | 20–30 |
| 14 | Levulinic | Oleic | cis-12-heneicosene-2-one | 125–135° | 1.4614 | 50–55 | 15–20 |
| 15 | 3-Acetoxy propionic | Oleic | 1-acetoxy-cis-10-nonadecene | 124–140° | 1.4525 | 45–50 | 5–8 |
| 16 | Succinic half methyl ester | Oleic | methyl-cis-11-eicoseneoate | 130–150° | 1.4540 | 45–50 | 8–10 |
| 17 | Acetic | Elaidic | trans-9-octadecene | [m. pt. 65–68°] | — | 70–75 | 8–12 |
| 18 | Propionic | Elaidic | trans-9-nonadecene | 125–135° | 1.4453 | 40–45 | 25–30 |
| 19 | Vinyl Acetic | Stearic | 1-eicosene | [m. pt. 53–54°] | — | 60–65 | — |
| 20 | Propionic | Linoleic | 6,9-nonadecadiene | 117–119° | 1.4587 | 50–55 | 15–20 |

EXAMPLE 21 - INSECT ACTIVITY TESTS

Products produced according to the invention were tested for activity towards the common house fly.

Bioassay of relative attractancy was determined in a laboratory olfactometer which consisted of a rectangular Plexiglass cage (15 × 50 cm) to which humidified outside air was delivered at a rate of about 300 ml/min: the air was passed through two trap-ports in the front face of the cage and exhausted by suction at the rear. Each port was a horizontal glass cylinder (15×3 cm) centered 9 cm apart and 3 cm below the top of the cage. The distal end of each port was connected to air-flow meters by a narrow glass sample tube (6×0.5 cm) containing cotton plugs. Test compounds were injected as 10 or 15 µl dosages into the sample tube plug of the test port; the other port was used exclusively as control with 0.5 ml of a 5% sucrose in milk solution.

Proximally, the ports were connected to the cage by glass connecting tubes (6×1.3 cm) with 3 cm of ech tube projecting freely past the neoprene bungs in each port (this prevented, to a large extent, responding flies from returning to the cage).

Forty to fifty virgin male flies, 4–5 days old, were used in each replicate with 2–4 replicates for each experimental compound. Each group of flies was used for only 2 or 3 tests with an intervening 2–4 hour recovery period, during which food (5% sucrose in milk) was supplied.

Three relatively distinct categories of behavioural response were recognized: a general excitement displayed as increased locomotory (running and flight) and cleaning activities; a strong sense of orientation towards the source of the attractant; and mating behaviour, where individuals made determined and repeated attempts to copulate with one another. These categories were arbitrarily quantified and recorded in Table II such as one (+) sign indicated observed response by about 25% of the individuals under test.

TABLE II

| Example No. | Compound cis-9-Alkene | Amount ($\mu l$) | Flies[a] Attracted to Test Compound | Control | Behavioural Response[b] Excitement (i) | Mating (ii) | Orientation (iii) |
|---|---|---|---|---|---|---|---|
| 1 | Mixture (3:7) of $C_{21}H_{42}$: $C_{23}H_{46}$ | 15 | 48 | 5 | ++++ | ++++ | − |
|  |  | 10 | 68 | 3 | +++ | +++ | + |
| 2 | Docosene, $C_{22}H_{44}$ | 10 | 48 | 4 | ++ | + | + |
| 3 | Tetracosene, $C_{24}H_{48}$ | 10 | 55 | 3 | +++ | − | + |
| 5 | Pentacosene, $C_{25}H_{50}$ | 10 | 12 | 3 | + | +− | + |
| 8 | Nonadecene, $C_{19}H_{38}$ | 10 | 23 | 12 | +− | − |  |
| 9 | Eicosene, $C_{20}H_{40}$ | 10 | 22 | 10 | +− | − | − |
| 10 | Heneicosene, $C_{21}H_{42}$ | 10 | 57 | 9 | + | + | +++ |
| 12 | Tricosene, $C_{23}H_{46}$ | 15 | 26 | 4 | +++ | +++ | − |
|  | "Muscalure" | 10 | 42 | 18 | ++ | + | + |
|  |  | 15 | 26 | 4 | +++ | +++ | − |
|  | 22-Methyl-cis-9-tricosene, $C_{24}H_{48}$ | 10 | 22 | 8 | + | +− | + |
|  | 20-Methyl-cis-9-eicosene, $C_{21}H_{42}$ | 10 | 20 | 4 | +− | +− | − |
|  | cis-9-10-epoxy-docosane, $C_{22}H_{44}O$ | 10 | 56 | 4 | ++ | ++ | ++ |

[a] in 30 minutes.
[b] + response by 25% individuals; −, no response.

The compound of Example 12 is identical with that which can be obtained from virgin female flies. The compound "Muscalure" is the product of the Wittig reaction and contains 15% trans-9-tricosene and 85% cis-9-tricosene.

What we claim as our invention is:

1. A long chain internal alkene selected from the group consisting of cis-9-docosene, cis-9-tetracosene, 2-methyl-cis-14-tricosene, 2-methyl-cis-15-tetracosene, cis-9-heneicosene, 2-methyl-cis-11-eicosene.

2. Cis-9-heneicosene.

* * * * *